(12) United States Patent
Watkins et al.

(10) Patent No.: US 7,135,023 B2
(45) Date of Patent: Nov. 14, 2006

(54) COMPRESSION BONE SCREW DEVICE

(76) Inventors: William T. Watkins, 12408 Carriage Trail, Davisburg, MI (US) 48350; Gary Wade, 7400 Jeffrey Ct., Linden, MI (US) 48451

( * ) Notice: Subject to any disclaimer, the term of this patent is extended or adjusted under 35 U.S.C. 154(b) by 90 days.

(21) Appl. No.: 10/884,207

(22) Filed: Jul. 2, 2004

(65) Prior Publication Data

US 2005/0010224 A1  Jan. 13, 2005

Related U.S. Application Data

(60) Provisional application No. 60/485,329, filed on Jul. 7, 2003.

(51) Int. Cl.
*A61B 17/58* (2006.01)
(52) U.S. Cl. .......................................... 606/65
(58) Field of Classification Search .......... 606/65–71; 623/23.11, 23.14, 23.26–27
See application file for complete search history.

(56) References Cited

U.S. PATENT DOCUMENTS

| | | |
|---|---|---|
| 2,496,129 A | 1/1950 | Haboush |
| 2,834,342 A | 5/1958 | Yost |
| 3,051,169 A * | 8/1962 | Grath .......................... 606/65 |
| 3,308,812 A * | 3/1967 | Gidlund ....................... 606/67 |
| 3,554,193 A * | 1/1971 | Konstantinou et al. ......... 606/65 |
| 4,095,591 A | 6/1978 | Graham, Jr. et al. |
| 4,129,903 A * | 12/1978 | Huggler .................... 623/23.11 |
| 4,172,452 A * | 10/1979 | Forte et al. .................. 606/67 |
| 4,612,920 A | 9/1986 | Lower |
| 4,621,629 A * | 11/1986 | Koeneman ................... 606/65 |
| 4,759,352 A * | 7/1988 | Lozier ........................ 606/66 |
| 4,795,473 A * | 1/1989 | Grimes .................... 623/23.11 |
| 4,988,350 A | 1/1991 | Herzberg |
| 5,007,935 A * | 4/1991 | Vincent et al. .......... 623/23.14 |
| 5,127,914 A * | 7/1992 | Calderale et al. ............. 606/65 |
| 5,462,547 A | 10/1995 | Weigum |
| 5,484,439 A * | 1/1996 | Olson et al. .................. 606/65 |
| 5,514,138 A * | 5/1996 | McCarthy ..................... 606/65 |
| 5,578,035 A * | 11/1996 | Lin .............................. 606/68 |
| 5,693,055 A * | 12/1997 | Zahiri et al. .................. 606/69 |
| 5,728,099 A * | 3/1998 | Tellman et al. ............... 606/65 |
| 5,749,872 A * | 5/1998 | Kyle et al. .................... 606/69 |
| 6,139,552 A * | 10/2000 | Horiuchi ...................... 606/88 |
| 6,383,227 B1 * | 5/2002 | Baroud et al. ............ 623/23.22 |
| 2001/0000186 A1 * | 4/2001 | Bramlet et al. ............... 606/66 |
| 2002/0049445 A1 * | 4/2002 | Hall et al. .................... 606/69 |

OTHER PUBLICATIONS

Michael R. Baugaertner, M.D., Compression Hip Screw Plates and Nails, Surgical Technique, Aug. 1998, Smith & Nephew, Inc.

* cited by examiner

*Primary Examiner*—Eduardo C. Robert
*Assistant Examiner*—Annette Reimers
(74) *Attorney, Agent, or Firm*—Young & Basile, P.C.

(57) ABSTRACT

A compression bone screw device for fixating a fractured bone. The device includes a constant compression lag screw, a side plate having a moveable rollerball for receipt of the lag screw and a compression member engageable with the lag screw and rollerball to impart a constant compressive force across the bone fracture.

3 Claims, 8 Drawing Sheets

COMPRESSION BONE SCREW DEVICE

CROSS-REFERENCE TO RELATED APPLICATIONS

This application claims benefit of the provisional patent application Ser. No. 60/485,329 filed Jul. 7, 2003 entitled Minimally Invasive Compression Hip Screw System. This claim is made under 35 U.S.C. § 119(e) and C.F.R. § 1.53(c)(3).

FIELD OF THE INVENTION

The present invention relates to orthopaedic surgical devices used to join and promote healing of fractured bone, and more particularly, and not by limitation, devices used to fixate proximal femoral fractures.

BACKGROUND OF THE INVENTION

Compression hip and bone screw devices for use in fixating a fractured bone during the healing process have been used for years. Referring to FIG. 1, the typical device 10 used for hip fractures uses a lag screw 22 that is inserted into a femur 12 and used with a fixed side plate 24 which is attached to the femoral shaft 16. The lag screw is secured in the femoral head 14 on one end and abuttingly engages the barrel on the other end using a compression member or screw 28 thereby placing the femoral head/neck in axial compression across a bone fracture 27 placing the separated portions of the femoral head, neck or shaft area in contact for healing of the fracture. See for example U.S. Pat. Nos. 4,612,920 and 5,484,439.

The typical hip screw 10 is installed in a patient by making a large incision in the patient adjacent the proximal femur or outer hip. A guide is used to angularly position a guide wire, commonly at 135° with respect to femoral shaft, to penetrate the cortex of the femur and drive the guide wire across the bone fracture to position the wire in the cancellous bone within the femoral head. Using the positioned guide wire, a drill is used to ream a hole in the cortex for receipt of the lag screw 22 and side plate barrel to extend through the cortex. The lag screw and side plate are inserted through the large incision with the guide wire directing the position the barrel and lag screw. The lag screw is inserted along the guide wire and threadingly secured in the femoral head. The side plate is secured to the femoral shaft and a compression screw 28 engaged on the exposed end of the lag screw 22 against the barrel to place the lag screw in tension and the fractured bone pieces in compression across the fracture.

The prior art devices and methods suffer from several disadvantages in installation, adjustability and short and long-term effectiveness. Prior art lag screw and adjoining compression screws may provide sufficient initial compression forces across the bone, but suffer the significant disadvantage of losing compressive force capability and effectiveness over a very short period of time through common bone resorption or actual shrinkage of the bone across the fracture during the initial phases of the bone healing process.

Prior art side plates and integral, fixed barrels suffer from disadvantages of requiring a long incision to accommodate the long, downstanding side plate along the femoral shaft and the angular oriented barrel 26 is fixed in the anterior, posterior, medial and lateral planes. The fixed angular orientation and close concentrical relationship between the barrel and lag screw provide little or no adjustment in the event of a malaligned lag screw or side plate. This can result in improper alignment of the lag screw in the side plate barrel which, over time, can loosen, cause cut-out of the lag screw in the femoral head, bind the lag screw in the barrel or cause improper transfer of load on the device. The long and fixed barrel 26 extending through the cortex requires a larger bore in the bone and increased trauma to the area.

Thus, it would be desirable to provide a compression bone screw device to improve on the prior art disadvantages. It is further desirable to provide a bone screw device having a constant compression lag screw to maintain compressive force on the fractured bone throughout the healing process and beyond. It is further desirable to provide a minimally invasive side plate having an adjustable rollerball for receipt and adjustable alignment of the lag screw and side plate to promote proper alignment, adjustability, performance and long-term life of the device. It is further desirable to provide a side plate that is contoured to femoral anatomy to more evenly distribute loads and having a reduced downstanding portion to minimize the length of the incision in the patient.

SUMMARY OF THE INVENTION

The present invention provides a compression bone screw device including a compression lag screw and complementary side plate having a rollerball for receipt, positional adjustability and installation of the compression lag screw.

The lag screw is preferably a constant compression lag screw including a lag screw having a threaded outer member and a separate inner member slideably engaged with the outer member portion and joined by a means for resisting separation of the members along a longitudinal axis. A compression barrel is threadingly engaged on the exposed end of the inner member adjacent the rollerball and on abutment with the rollerball, exerts a force against the resistance means along the longitudinal axis placing the lag screw in constant tension providing constant compression across the bone fracture.

The side plate includes a base plate having a shape complementary to the bone and a rollerball positioned toward a central portion of the base plate. The rollerball provides for controlled, multidirectional movement for aligned and concentrical receipt of the constant compression lag screw. On installation of the compression barrel, stops on the rollerball prevent further movement of the rollerball and lag screw with respect to the side plate The side plate includes several apertures positioned above and below the rollerball for use of bone screws to attach the side plate to the bone.

In one aspect, the constant compression lag screw uses a tension spring as the resistance means and in an alternate aspect, uses a fluid chamber instead of a mechanical spring.

Other applications of the present invention will become apparent to those skilled in the art when the following description of the best mode contemplated for practicing the invention is read in conjunction with the accompanying drawings.

BRIEF DESCRIPTION OF THE DRAWING

The description herein makes reference to the accompanying drawings wherein like reference numerals refer to like parts throughout the several views, and wherein.

DETAILED DESCRIPTION OF THE PREFERRED EMBODIMENT

Figure 2:
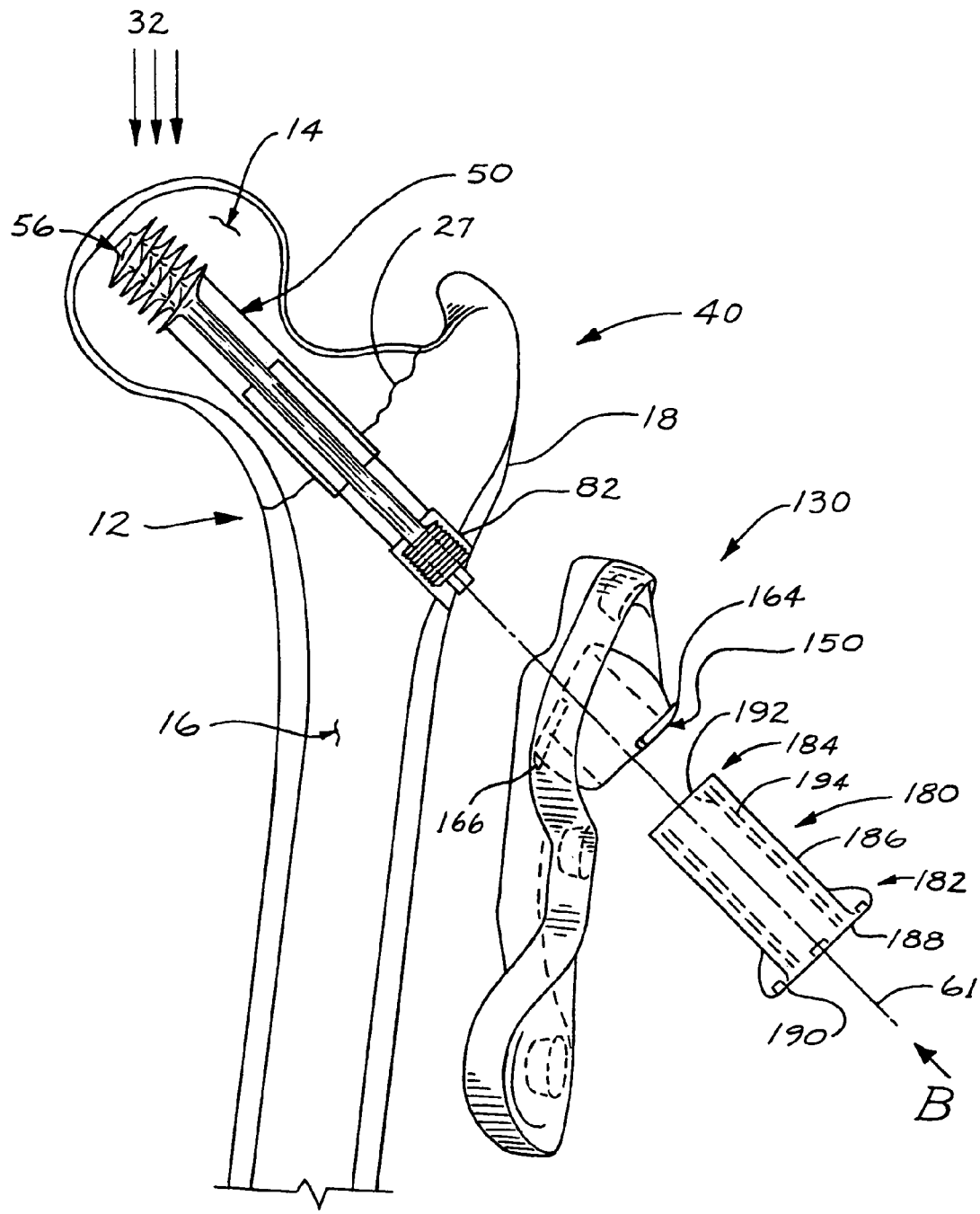
FIG. 2 is a frontal exploded view of a compression bone screw device of the present invention illustrating an embodiment for use as a hip screw.

Referring to FIGS. 2–13, the preferred embodiment of a compression bone screw device is illustrated. Referring to FIG. 2, a preferred, but not exclusive application of the present invention is to repair a fracture 27 in a human femur 12 having a femoral head 14 and a femoral shaft 16. The aspect illustrated includes a constant compression lag screw 50, a side plate 130 with a rollerball 150 and compression barrel 180. It is understood that the present invention is usable in other applications other than as a compression hip screw as explained below.

Figure 3:
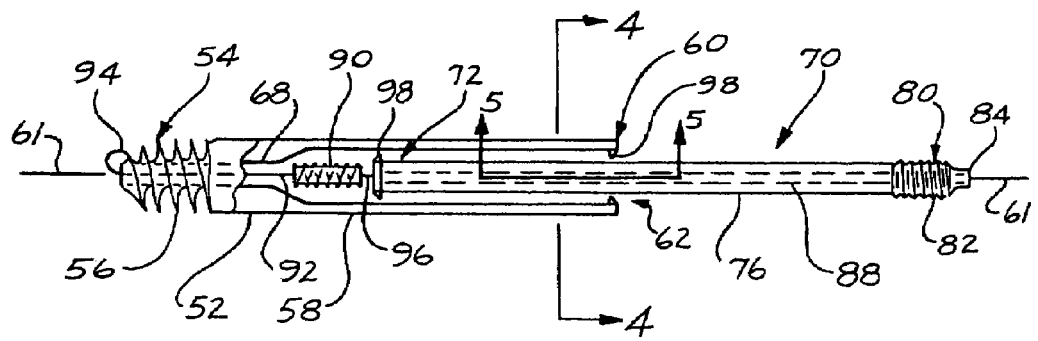
FIG. 3 is a partially cut-away view of one embodiment of a constant compression lag screw.
Figure 4:
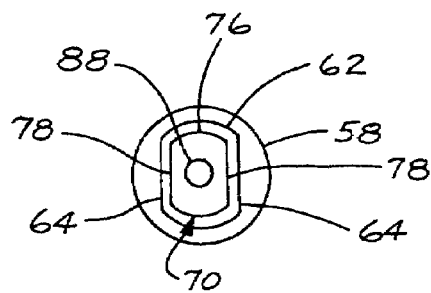
FIG. 4 is a cross sectional view taken along lines 4—4 in FIG. 3.

Referring to FIGS. 2–4, a constant compression lag screw 50 is illustrated. Referring to FIGS. 3 and 4, a constant compression lag screw 50 includes an outer member 52 having a first end 54 with coarse threads 56. Threads 56 may vary in thread size and pitch and are suitable for threading and secure engagement of the lag screw in the femoral head as shown in FIG. 2 or to suit the particular application. Lag screw outer member 52 further includes an outer surface 58 having a second and open end 60 defining an elongate first bore 60 extending along the longitudinal axis 61 of the outer member 52 as shown in FIG. 3. As best seen in FIG. 4, first bore 62 is generally circular-shaped and includes means for preventing rotation of outer member 52 with respect to inner member 70 described below in the form of one or more flat surfaces 64 on opposing sides. It is understood that the flat surfaces 64 may be more or less then two in number and may take any shape or polygonal form. Outer member 52 further includes a second elongate bore 68 adjacent to first end 54 and in communication with first bore 62. Second bore 68 extends through first end 54 forming a continuous bore or cannulation through first member 52.

Constant compression lag screw 50 further includes an inner member 70 as best seen in FIG. 3. Inner member 70 includes a first end 72 preferably positionable within first bore 62 of outer member 52. Inner member 70 further includes an outer surface 76 complementary to outer member bore 62 including flat surfaces 78 as best seen in FIG. 4. Inner member 70 further includes a second end 80 including a threaded portion 82 and a head 84 extending along the longitudinal axis 61 of inner member 70 as best seen FIG. 3. Threaded portion 80 is typically fine machine threads, but may take any suitable thread or connection type to suit the particular application. Head 84 is preferably a six-sided hex head suitable for receiving a medical wrench or socket tool for rotation of the inner member 70 and the lag screw 50. It is understood that head 84 can take many additional forms known by those skilled in the art including an aperture extending into head 84 along the longitudinal axis of inner member 70 suitable for receiving an allen-type wrench or other rotational drive tool.

Inner member 70 further includes a through bore 88 extending along the entire longitudinal axis 61 of inner member 70 in alignment and communication with first 62 and second 68 bores in outer member 52 as best seen in FIGS. 3 and 4. Inner member 70 is preferably slidingly received and moveable within first bore 62 of outer member 52 along the longitudinal axis 61. Although illustrated as inner member 70 slideably received in outer member 52, it is understood that in an alternate aspect, outer member 52 may be received in inner member 70 in a similar fashion (not shown).

Inner member 70 and outer member 52 are preferably fabricated from medical grade stainless steel or titanium but may be made from other materials suitable for the particular application as known by those skilled in the art.

Constant compression lag screw 50 further includes a means for resisting extraction or separation of inner member 70 from outer member 52 along the longitudinal axis 61 of lag screw 50. In a preferred aspect, the means for resisting separation includes a tension spring 90 having a first end 92 positioned toward first end 54 of outer member 52. In a preferred embodiment, first end 92 extends through second bore 68 and protrudes out of first end 54 having a hook 94 to engage the exterior of first end 54 as shown in FIG. 3. An adhesive or other means to secure hook 94 to first end 54 may be used such as welding or other mechanical or physical means. It is further understood that spring first end 92 may be attached internally at a point along second bore 68 by similar or other means known by those skilled in the art (not shown).

Tension spring 90 further includes a second end 96 extending along longitudinal axis 61 and is connected to first end 72 of inner member 70. Second end 96 may be connected to inner member 70 through similar mechanical, chemical or other means known by those skilled in the art. Although the resistance means is illustrated as a tension spring, it is understood that other mechanical means may be used, for example only, a compression spring, elastomeric materials, controlled friction between opposing surfaces, and other means for providing resistance known by those skilled in the art.

Referring to FIG. 3, constant compression lag screw 50 further preferably includes stops 98 positioned on first end 72 of inner member 70 and second end 60 of outer member 52. Stops 98 deter or prevent unauthorized removal or over distraction of inner member 70 from outer member 52 through abutting engagement. Stops 98 may be positioned at selected areas on outer surface 58 and first bore 62 or may be positioned around the circumferences thereof. It is also understood that stops 98 may be positioned anywhere along outer surface 76 and first bore 62 to suit the particular application and separation considerations.

Figure 15:
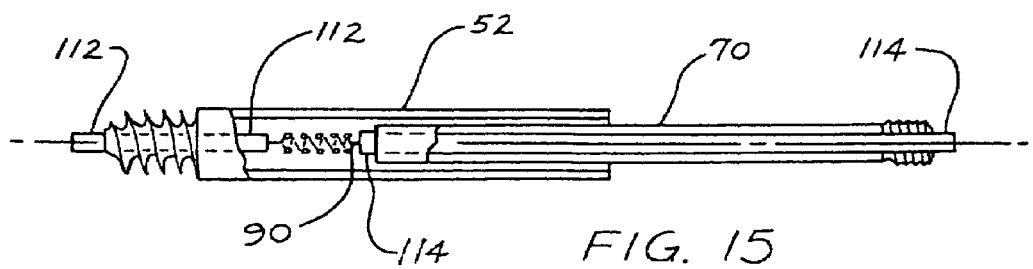
FIG. 15 is a partially cut-away view of an alternate embodiment of a constant compression bone screw shown in FIG. 3.

Referring to FIG. 15, an alternate aspect of the resistance means is shown. In this aspect, spring 90 is attached to a first cannulated sleeve 112 extending through first end 54 and a second cannulated sleeve 114 that is positioned in bore 88 of inner member 70 and extends through head 84. On insertion of first 112 and second 114 sleeves and spring 90 into inner 70 and out 52 members as shown, the exposed ends are secured to first end 54 and 84 through one of a variety of mechanical means, for example, cold heading, welding or bending around to prevent the tensioned spring from pulling the exposed end back inside (not shown). Other methods of attachment means know by those skilled in the art may also be used.

Figure 5:
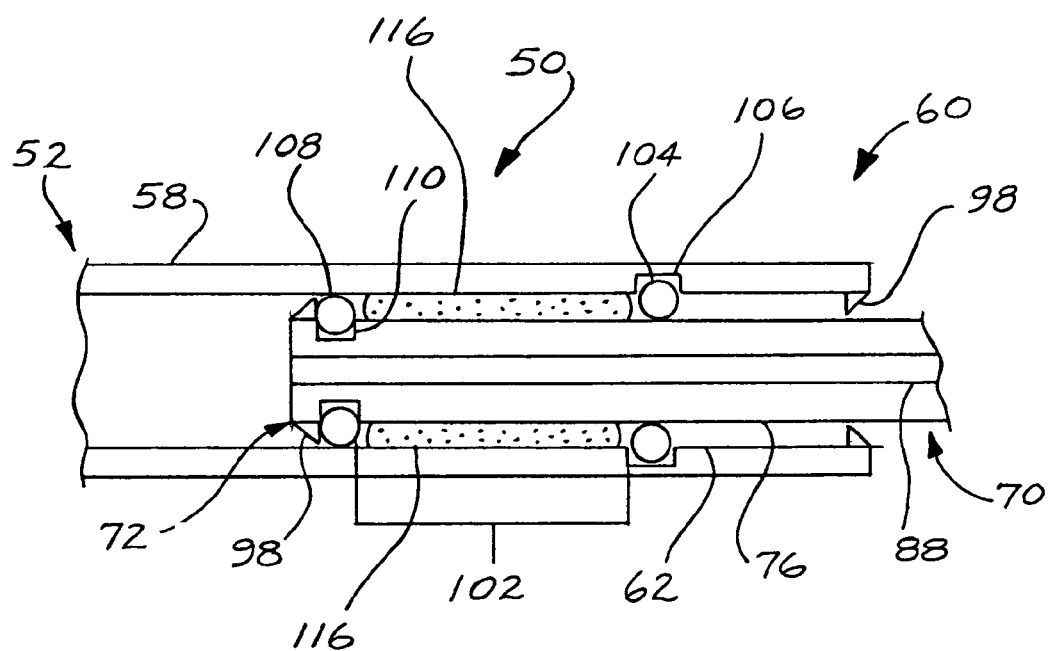
FIG. 5 is an alternate embodiment cross-sectional view taken along line 5—5 in FIG. 3.

Referring to FIG. 5, an alternate embodiment of the means for resisting separation of outer member 52 from inner member 70 is shown. Replacing the mechanical tension spring 90 is a fluid compression chamber 102 formed between outer surface 76 of inner member 70 and first bore 62 of outer member 52. In the alternate aspect, fluid chamber 102 is defined by a first seal 104 positioned in first channel 106 in the wall of outer member 52 as best seen in FIG. 5. Seal 104 is preferably an elastomeric O-ring seal positioned in first channel 106 and sealingly engages outer surface 76 of inner member 70. Fluid chamber 102 is further defined by a second seal 108 positioned in second channel 110 which sealing engages outer member 52 in a similar fashion. Chamber 102 preferably includes a sealed container 116 filled with a sterile fluid either in liquid, for example saline, or gas. The container 116 is preferably installed around inner member 70 as the inner member 70 is positioned in outer member 52. Once installed, on extraction or removal forces applied to inner member 70 to separate inner 72 from outer member 52, along longitudinal axis 61, sealed container 116 is compressed and resistance is generated from further extraction of inner member 70 from outer member 52 along the longitudinal axis 61 of lag screw 50.

Figure 6:
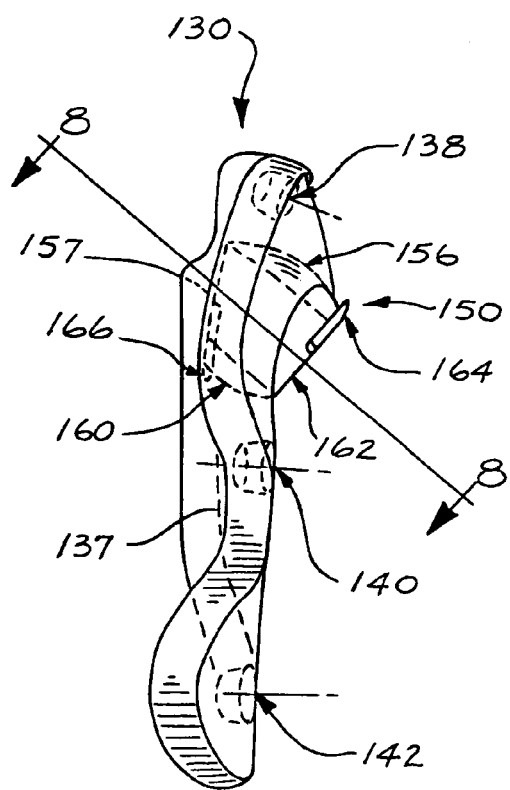
FIG. 6 is a frontal view of a bone screw side plate illustrating an embodiment used as a hip screw.
Figure 7:
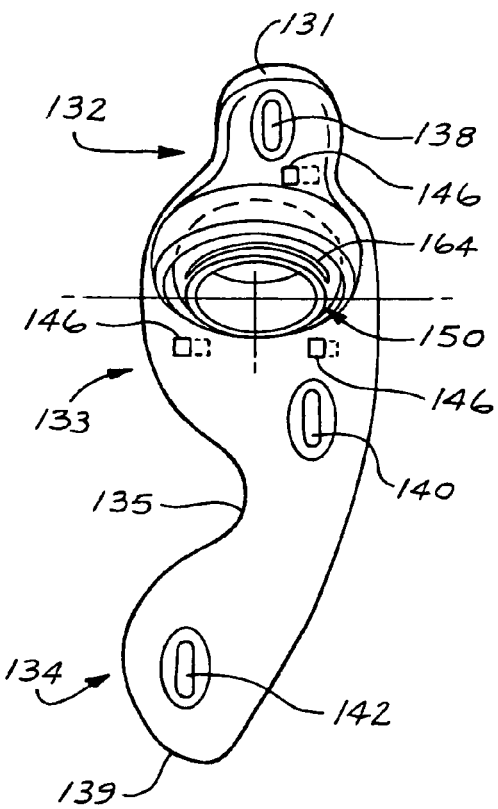
FIG. 7 is a side view of the side plate shown in FIG. 6.

In a preferred use of the invention as a hip screw device, constant compression lag screw 50 is used with a side plate 130. As shown in FIGS. 2, 6 and 7, side plate 130 includes and upper portion 132, an upper edge 131, a central portion 133, a lower portion 134, a lower edge 139, a front surface 136, and back surface 137 as best seen in FIGS. 6 and 7. Upper portion 132 is positioned at an angle to central 133 and lower portion 134 as best seen in FIGS. 2 and 6 to accommodate the flare of the greater trochanter 18. Central 133 and lower 134 portions are generally planer and back surface 137 is generally concave to generally conform to the round or convex shape of the outer cortex of femoral shaft 16 as best seen in FIGS. 2 and 6. Side plate 130 further includes locking apertures 146 as shown in FIG. 7.

Referring to FIG. 7, the perimeter of side plate 130 is rounded in form and includes at least one notch 135 to reduce material and weight while preserving strength and general conformity with femur 12. It is understood that different perimeter shapes and configurations may be used without departing from the present invention.

Side plate 130 further includes a first aperture 138, a second aperture 140 and third aperture 142 for mounting of the side plate to a femoral shaft 16 or other bone. In a preferred aspect, at least one of the apertures is positioned above the rollerball. It is understood the number and location of the holes may vary to suit the particular application without deviating from the present invention.

Figure 8:
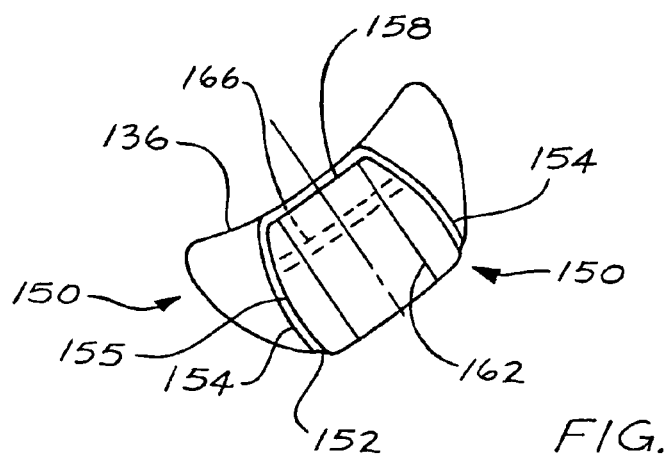
FIG. 8 is a cross sectional view taken along line 8—8 in FIG. 6.

Side plate 130 preferably includes an integral roller ball 150 movably mounted in a central aperture 152 as best see in FIGS. 6 through 8. Roller ball 150 includes a generally spherical-shaped outer surface 155 including an upper portion 156 and a lower portion 160 in slideable engagement with concave-shaped surfaces 154 in side plate 150 as best see in FIG. 8. Rollerball 150 includes a tapered back surface 157. On a press-fit insertion of rollerball 150 into central aperture or through other securement methods, concave surfaces 154 confine roller ball 150 in side plate 130 preventing unauthorized removal of roller ball 150 while permitting multi-axis rotation and movement of roller ball 150 with respect to side plate .130.

Roller ball 150 further includes a through bore 162 in axial alignment with central aperture 152 in side plate 130. Roller ball 150 preferably includes an upper stop 164 and lower stop 166 which on abutting engagement with side plate 130 provide maximum limits of movement of rollerball 150 with respect to side plate 130 within a desired range as best seen in FIG. 6. In an installed position with lag screw 50 and compression barrel 180 described below, upper 164 and lower 166 abuttingly engage side plate 130 preventing further upward rotation of rollerball 150 with respect to side plate 130. Rollerball through bore 162 is positioned in substantially axial alignment with longitudinal axis 61 of the constant compression lag screw 50 as best seen in FIG. 2.

Figure 1:
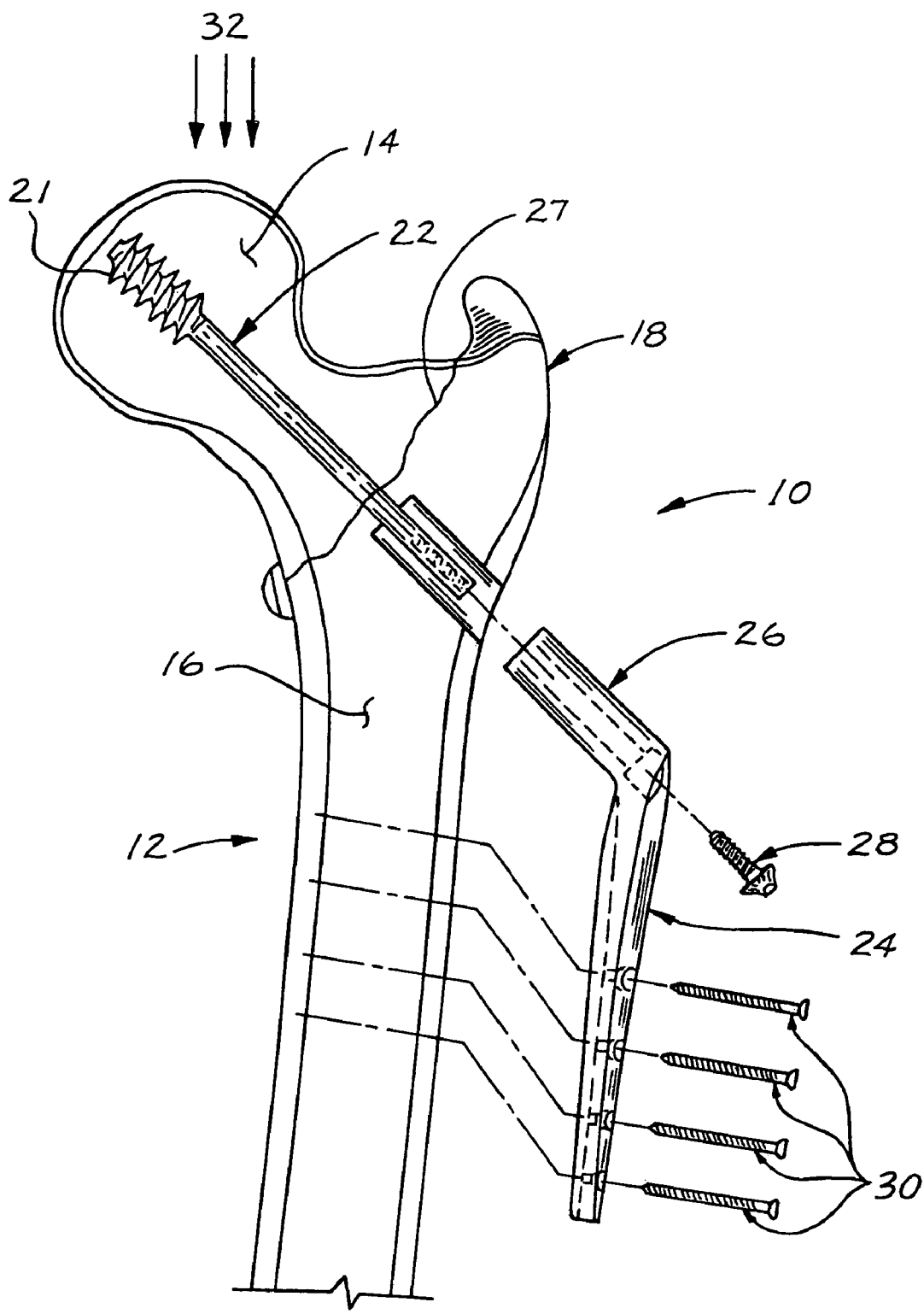
FIG. 1 is a frontal exploded view of a typical prior art hip screw device including a lag screw, a compression screw and a side plate.

Central aperture 152 and rollerball 150 are preferably positioned toward the central portion 133 between upper edge 131 and lower 139 edges of side plate 130 to distribute the load forces 32 placed on femur 12 both above and below the roller ball 150 in contrast to typical hip screw designs as general shown in FIG. 1. The inventive side plate configuration provides more even distribution of the load on side plate 130 and femur 12. Side plate 130 and rollerball 150 are fabricated from medical grade stainless steel or other materials to suit the particular application as known by those skilled in the art.

Figure 13:
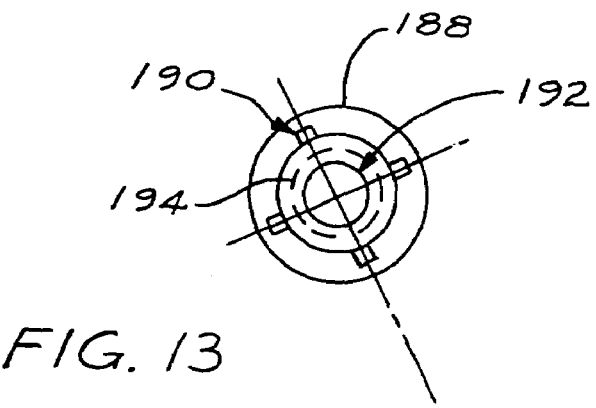
FIG. 13 is directional view taken along line B in FIG. 2.

Referring to FIGS. 2 and 13, a preferred compression barrel 180 is illustrated. Compression barrel 180 includes a first end 182, a second end 184 and an outer surface 186. Compression barrel 180 further includes an enlarged head 188 greater in diameter than rollerball bore 162 having a plurality of notches 190 and a through bore 192. A portion of through bore 192 adjacent second end 184 includes threads complementary to and threadingly engagable with threads 82 of inner member 70 of compression lag screw 50.

As best seen in FIG. 13, notches 190 are provided for an insertion tool to grasp and rotate compression barrel 180 for threading engagement with compression lag screw 50. Outer surface 186 is smaller in diameter than rollerball bore 162 permitting sliding and rotational movement of compression barrel 180 in rollerball 150 without an interference or too loose a fit. Enlarged head 188 is sufficiently larger than bore 162 such that compression barrel 180 cannot pass all of the way through rollerball 150 but rather, abuts rollerball 150 preventing further axial translation through rollerball 150. Through multi-axis movement capability of rollerball 150, compression barrel 180 and threadingly engaged compression lag screw 50 are translatable through selected and controlled movement of rollerball 150 with respect to side plate 130. Compression barrel 180 is preferably manufactured from medical grade stainless steel or titanium but other materials may be used to suit the particular application.

Figure 11:
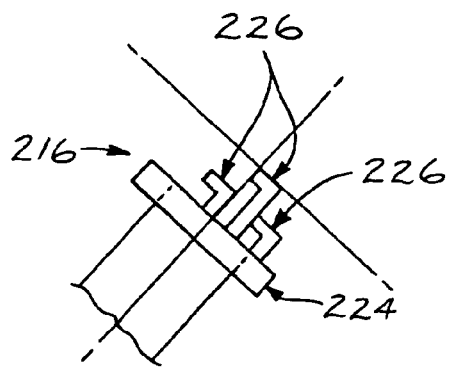
FIG. 11 is a partial frontal view of FIG. 9 illustrating an embodiment of an insert handle.
Figure 10:
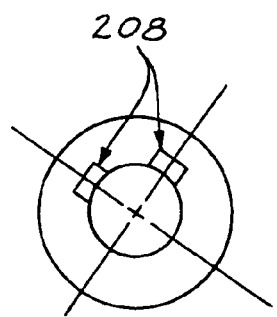
FIG. 10 is a directional view of a portion of an insert handle taken along line A in FIG. 9.
Figure 9:
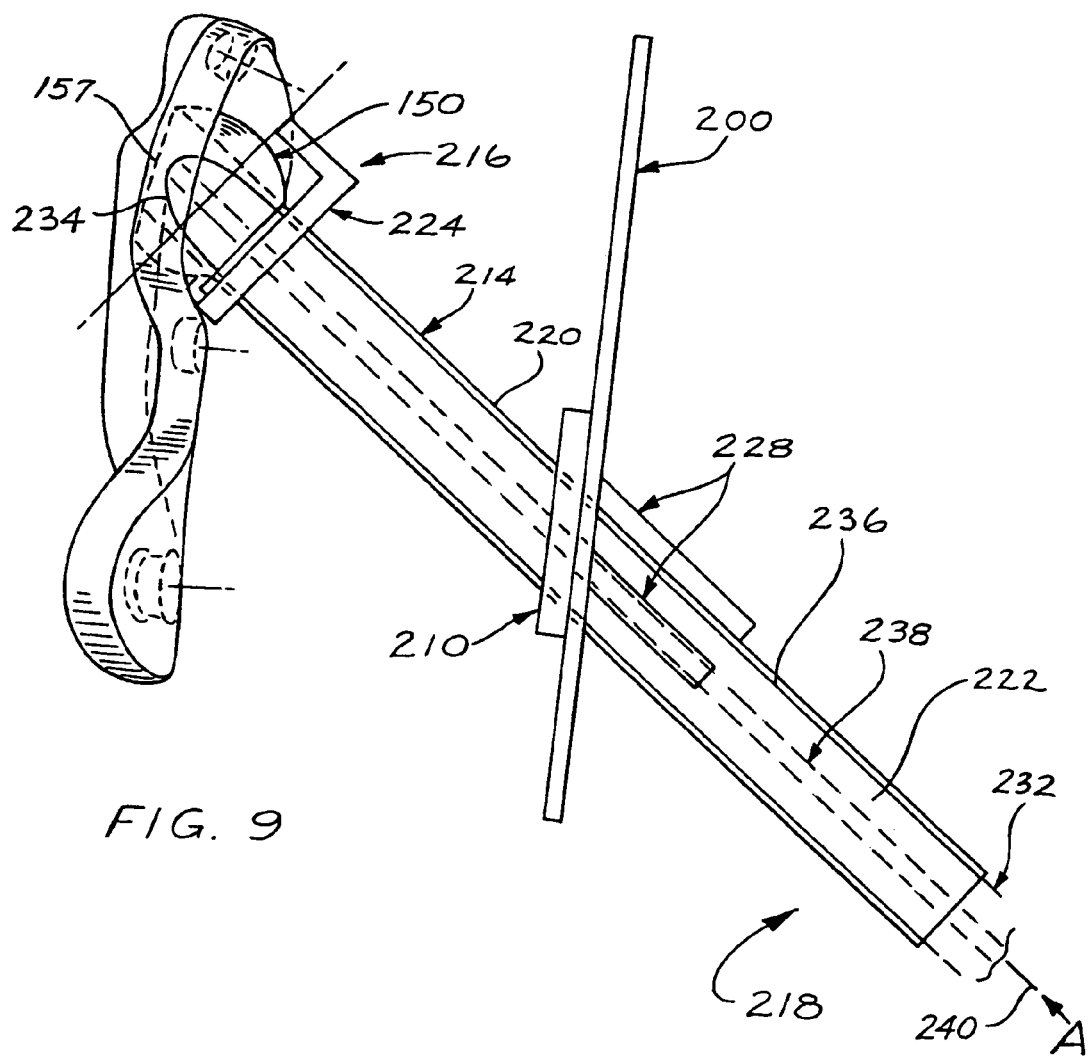
FIG. 9 is a frontal view of an embodiment illustrating use of an insertion tool to position the side plate shown in FIG. 6.

Referring to FIGS. 9–12, a preferred insertion tool 214 is shown. Insertion tool 214 is engageable with side plate 130 in locking apertures 146 for positioning and installing side plate 130 in a patient. Referring to FIGS. 9–11, insertion handle 214 includes a first end 216, a second end 218, an intermediate portion 220, and through bore 222. Insertion handle 214 includes a flange 224 adjacent the first end 216 extending radially outward from a longitudinal axis of insertion handle 214 as best seen in FIGS. 9 and 11. Flange 224 includes a plurality of offset locking tabs 226 shown in FIG. 11 which frictionally engage locking apertures 146 shown in FIG. 7 positioned on side plate 130. Insertion handle 214 includes keys 228 positioned on the outside surface of intermediate portion 220 angularly offset from one another and complementary to keyways 208 on the template plate 220 and stop ring 210 discussed below. See FIG. 10.

Insertion handle 214 further preferably includes an insertion handle sleeve 232 positioned concentrically within insertion handle 214 as best seen in FIG. 9. Insertion handle sleeve 232 includes a first convex end 234 adjacent the first end 216 of insertion handle 214 and includes a shaft 236 and a through bore 238 extending along the longitudinal axis of the sleeve throughout the length of insertion handle sleeve 232. First end 234 is sized to be positioned in rollerball bore 162 as best seen in FIG. 9.

Figure 12:
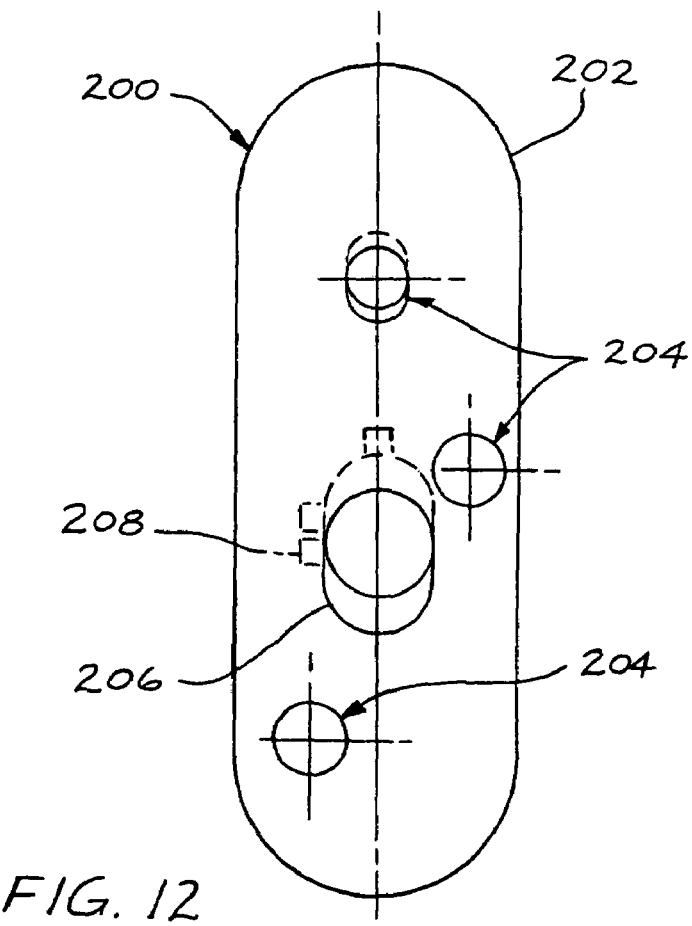
FIG. 12 is a side view of an installation template as schematically illustrated in FIG. 9.

Insertion handle 214 may be used with an installation template 200 as best seen in FIG. 12. Installation template 200 includes a plate 202 which is generally planer or rounded and includes mounting screw apertures 204 positioned in axial alignment with and which are used to install bone screws (not shown in FIG. 9) through mounting apertures 138, 140 and 142 in side plate 130. Template plate 202 further includes a central aperture 206 for insertion and passage through of insertion handle 214. As best seen in FIG. 12, mounting guide apertures 204 and central aperture 206 are positioned in template 202 at an angle as best seen in FIG. 9, commonly, but not limited to 135° in alignment with the angle of lag screw 50 with respect to side plate 130. Central aperture 206 includes a plurality of keyway apertures 208 as best seen in FIG. 12. Installation template 200 further includes a stop ring 210 positioned on the medial or interior side of template plate 202 as best seen in FIG. 9.

In operation, on a need for installation of the inventive compression bone screw device to fixate a fracture, an incision in made in a patient adjacent the femoral cortex. The size of the side plate 130 enables a much smaller incision than typical prior art hip screw mounting plates as shown in FIG. 1. Insertion handle 214 is positioned so that locking tabs 226 are axially aligned with locking apertures 146 in side plate 130. Insertion handle 214 is rotated such that locking tabs 226 frictionally engage locking apertures 146. Insertion handle 214 is rotated such that locking tabs 226 frictionally engage locking apertures 146 in side plate 130. On frictional engagement of locking tabs 226 in locking apertures 146, insertion handle 214 is firmly secured to the side plate 130. Insertion handle sleeve 232 is inserted into and through insertion handle 214 such that conical first end 234 is positioned inside of rollerball bore 162 temporarily fixing the position of rollerball 150 with respect to side plate 130 and handle 214, as best seen in FIG. 9. In this position upper 164 and lower 166 stops are in contact with side plate 130 thereby preventing further upward rotation of rollerball 150 and cantilever forces on the bone fracture, for example, fracture 27. The insertion handle 214 and side plate are inserted into the patient adjacent the femur 12 positioning side plate upper portion 132 against the flare of the greater trochanter 18 as shown in FIG. 2.

A guide wire 240 is inserted through the handle sleeve bore 238 and rollerball bore 162 and is used to pierce the cortex of the lateral femur 12 at the predetermined angle, for example 135°, and is lodged in the upper portion of the femoral head 14 across the fracture, for example, across the femoral neck. Bone screws 30 may be used to secure the side plate 130 to the femoral shaft 16 or left unsecured until the compression lag screw 50 and compression barrel 180 are installed as described below. The sleeve 232 is then removed and a cannulated bone reamer is positioned over the guide wire 240 to ream a bore through the cortex for clearance for the compression lag screw 50. As best seen in FIG. 2, the preferred constant compression lag screw 50 is axially inserted through insertion handle bore 222 and rollerball bore 162 along the guide wire positioning the outer member 52 and threads 56 in the femoral head 14. A T-handle or other wrench is engaged with inner head 84 for rotation of lag screw 50 to secure lag screw 50 in femoral head 14 as seen in FIG. 2.

The compression barrel 180 is engaged with the constant compression lag screw 50 through threading engagement with threads 82 of inner member 70.

The side plate 130 may be mounted to the femoral shaft 16 through bones screws 30 through insertion template 200 mounting apertures and through first 138, second 140 and third 142 mounting apertures in side plate 130. Through engagement and rotation of compression barrel 180, compression barrel 180 is progressively threaded along inner member 70 until enlarged head 188 abuts rollerball 150. Further rotation of compression barrel 180 with inner member 70 extends tension spring 90 thereby placing constant compression lag screw 50, and more particularly, inner member 70 and outer member 52 in tension thereby drawing the fractured bones pieces together and placing the fracture 27 in compression. Compression barrel 180 is further rotated until the desired tension in compression lag screw 50 and compression across the fracture is achieved. In this position rollerball upper 164 and lower 166 stops are abuttingly engaged with side plate 130 preventing further upward rotation of rollerball 150. Insertion handle 214 is removed from side plate 130 by rotating the handle in the opposite direction thereby relieving the frictional engagement of handle 214 from side plate 130 and the insertion handle is removed from the patient. In an alternate aspect, the side plate 130 may be secured to the femoral shaft prior to installation and securement of the lag screw 50 and compression barrel 180.

During the healing process and beyond, the compression lag screw resistance means maintains tension between the outer member 52 and the inner member 70 thereby continuing a substantially constant compression force across the fracture 27 to minimize the effects of resorption on the compression bone screw device for improved healing of the fractured joint and providing additional support beyond the healing period.

On normal loading 32 of the femoral head, the load forces 32 are transferred through the constant compression lag screw 50, rollerball 150 and side plate 130 and are managed through the side plate into the femoral shaft 16 both above rollerball 150, pressing the side plate upper portion 132 against the flare of the greater trochanter, and below rollerball 150, distributing the forces through bone screws 30, providing a stronger and more robust repair and long term bone support.

Figure 14:
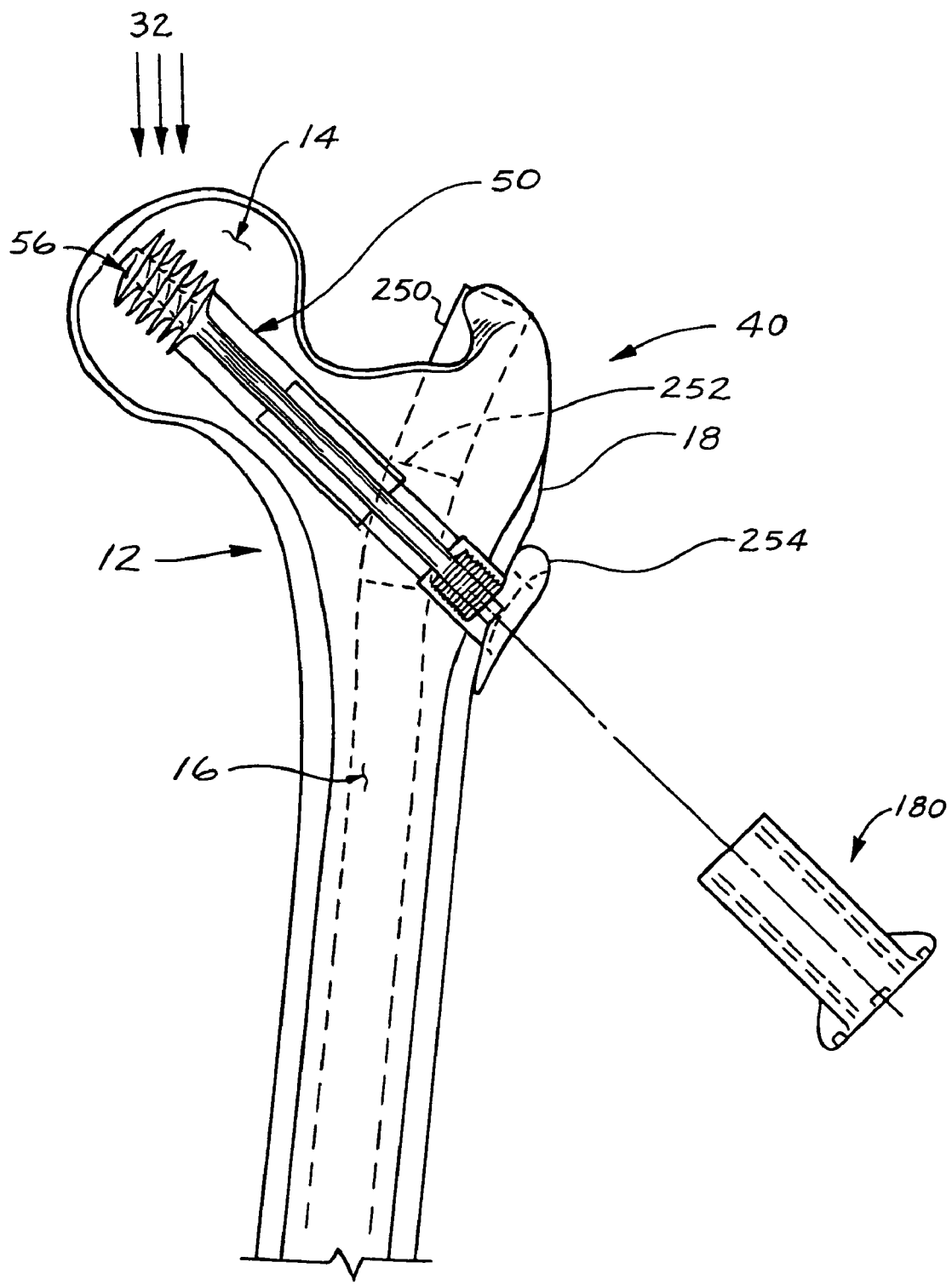
FIG. 14 is a frontal exploded view of an alternate embodiment of the compression bone screw device shown in FIG. 2.

Although illustrated as useful in a hip screw application, it is understood that the inventive device may be used in other applications. It is further understood that constant compression lag screw 50 may be used in other applications independently of the side plate 130 in a application where a side plate is not required, for example, in an intermedular hip screw application as shown in FIG. 14. In this aspect, a rod 250 is positioned through the femoral shaft and includes a bore 252. A constant compression lag screw 50 is positioned across the fracture as previously described and a spacer 254 is positioned on the cortex as shown and receives the compression barrel 180.

It is further understood that the constant compression lag screw 50 may be used independently without side plate 130 or spacer 254 as a canulated, constant compression bone screw. It is further understood that side plate 130 with moveable rollerball 150 may be used independently of constant compression lag screw 50. For exemplary purposes, side plate 130 may be used with a conventional lag screw 22 and compression member or screw 28 shown in FIG. 1.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A constant compression bone screw comprising:
   An elongate outer member having a first end and a second end defining an elongate bore and a longitudinal axis,
   an inner member positioned in the elongate bore along the longitudinal axis having a first end and second end,
   means engagable with the inner member and the outer member for resisting axial separation of the inner member with respect to the outer member along the longitudinal axis comprising a first channel in the inner member and a second channel in the outer member distant from the first channel along the longitudinal axis and a seal positioned in the first channel and the second channel between the inner member and the outer member defining a sealed chamber positioned between the inner member and the outer member, and
   means for preventing rotation of the inner member with respect to the outer member about the longitudinal axis.

2. A constant compression bone screw comprising:
   An elongate outer member having a first end and a second end defining an elongate bore and a longitudinal axis,
   an inner member positioned in the elongate bore along the longitudinal axis having a first end and second end,
   means engagable with the inner member and the outer member for resisting axial separation of the inner member with respect to the outer member along the longitudinal axis comprising a first channel in the inner member and a second channel in the outer member distant from the first channel along the longitudinal axis and a seal positioned in the first channel and the second channel between the inner member and the outer member defining a sealed chamber positioned between the inner member and the outer member, the sealed chamber further comprising at least one of a fluid and a gas which provides a resistive force against separation of the inner member from the outer member along the longitudinal axis; and
   means for preventing rotation of the inner member with respect to the outer member about the longitudinal axis.

3. A compression bone screw device comprising:
   a constant compression bone screw having an elongate outer member having a first end and a second end defining an elongate bare along a longitudinal axis, a separate inner member concentrically positioned in the outer member elongate bore along the longitudinal axis, the bone screw further comprising a means engaged with the inner member and the outer member for resisting separation of the inner member from the outer member along the longitudinal axis and an abutment surface on the inner member for preventing rotation of the inner member with respect to the outer member about the longitudinal axis;
   the means for resisting separation comprising a sealed chamber positioned in the outer member elongate bore defined by the outer member, the inner member and a seal between the inner member and the outer member, the resisting means includes at least one of a liquid and a gas in the sealed chamber providing a resisting force against separation of the inner member from the outer member along the longitudinal axis;
   a side plate having a rollerball movable with respect to the side plate, the rollerball having a bore adapted to be positioned in axial alignment with the longitudinal axis; and
   a compression barrel positioned in the rollerball bore adapted to engage one of the inner member and the outer member, the barrel abuttingly engaging the rollerball to forceably separate the inner member from the outer member along the longitudinal axis against the resisting means.

* * * * *